US007595188B2

(12) United States Patent
Hasegawa et al.

(10) Patent No.: US 7,595,188 B2
(45) Date of Patent: Sep. 29, 2009

(54) OBSERVATION APPARATUS

(75) Inventors: Kazuhiro Hasegawa, Tokyo (JP); Akitsugu Kagayama, Tokyo (JP); Hideaki Endo, Tokyo (JP); Ryuichi Hirano, Tokyo (JP); Atsuhiro Tsuchiya, Tokyo (JP); Kenichi Koyama, Tokyo (JP); Katsuyoshi Yamaguchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 645 days.

(21) Appl. No.: 11/302,591

(22) Filed: Dec. 12, 2005

(65) Prior Publication Data
US 2006/0128005 A1 Jun. 15, 2006

(30) Foreign Application Priority Data
Dec. 14, 2004 (JP) .............................. 2004-361784

(51) Int. Cl.
*C12M 3/00* (2006.01)
(52) U.S. Cl. .............. 435/286.2; 435/287.3; 435/288.7; 422/63; 422/64
(58) Field of Classification Search .............. 435/286.2, 435/287.3; 359/198.1, 200.1, 200.2, 896
See application file for complete search history.

(56) References Cited

U.S. PATENT DOCUMENTS 2,120,404 A 6/1938 Graff 3,997,404 A 12/1976 Waters
4,775,628 A * 10/1988 Takakura et al. ......... 435/305.4
5,134,070 A 7/1992 Casnig
6,219,180 B1 * 4/2001 Hasegawa et al. ........... 359/387
2002/0131167 A1 9/2002 Nguyen et al.
2005/0105172 A1 * 5/2005 Hasegawa et al. ........... 359/368

FOREIGN PATENT DOCUMENTS

| DE | 33 20 819 A1 | 2/1984 |
| DE | 3320819 A1 * | 9/1984 |
| EP | 0 896 238 A2 | 2/1999 |
| GB | 699059 | 10/1953 |
| JP | 09-318506 * | 12/1997 |
| JP | 11-202213 A | 7/1999 |

OTHER PUBLICATIONS

Machine translation DE 3320819 A1.*
Machine translation JP 09318506.*

* cited by examiner

*Primary Examiner*—William H Beisner
*Assistant Examiner*—Michael Hobbs
(74) *Attorney, Agent, or Firm*—Frishauf, Holtz, Goodman & Chick, P.C.

(57) ABSTRACT

An observation apparatus includes a sample tray that holds a container housing a cultured cell and a culture medium and covered with a lid; an observation unit that serves for observation of the cultured cell; and a shifting unit that relatively shifts the sample tray and a light axis of the observation unit along a plane that is orthogonal to the light axis of the observation unit, wherein the sample tray includes a container holding unit that holds the container by utilizing an elastic force, and at least one of the lid and one portion of the lid is made detachable, with the container being held in the sample tray by the container holding unit.

6 Claims, 7 Drawing Sheets

OBSERVATION APPARATUS

CROSS-REFERENCE TO RELATED APPLICATIONS

This application is based upon and claims the benefit of priority from Japanese Patent Application No. 2004-361784, filed on Dec. 14, 2004, the entire contents of which are incorporated herein by reference.

BACKGROUND OF THE INVENTION

1. Field of the Invention

The present invention relates to an observation apparatus used for observing a cultured cell.

2. Description of the Related Art

In the field of biological research, various experiments have been conducted with the use of cultured cells for the study of dynamic changes in living organisms. The cultured cells are placed in a carbon dioxide incubator that is kept at an inner temperature of 37° C., a carbon dioxide gas concentration of 5%, and a humidity of 100%, together with a liquid referred to as a culture medium made from bovine serum or the like, so that the activities of the cultured cells are maintained. Moreover, observation apparatuses, which allow observation while the activities of the cultured cells are maintained with the use of a microscope equipped with functions of the carbon dioxide incubator, have been commercially available.

Cultured cells and a culture medium are generally cultured in a dish that is made of plastic or glass and has a cylindrical form in its outer shape or a petri dish which is available in various shapes. Upon observation under the microscope, the use of an appropriate holder with a suitable shape for the container is required. Otherwise, the observable area may be limited or the container may fall onto the microscope.

For this reason, Japanese Patent Application Laid-Open (JP-A) No. H11-202213 proposes a sample holder capable of holding petri dishes of various sizes and shapes with the use of a movable petri dish holder.

Some experiments using such cultured cells last a long period of time, in particular, experiments on cell lineage, in which changes in specific cells are traced, is carried out over a long period of time.

The culture medium, however, needs to be changed once approximately every three days. Hence, the long-term observation of a specific cell necessarily accompanies the exchange of culture mediums, which is carried out on a clean bench or the like after the removal of the container containing cultured cells from the microscope.

In JP-A No. H11-202213, though the petri dish can be held with the use of the shiftable petri dish holder, it is difficult to position the petri dish within a range of approximately 5 μm that is required for a high-magnification observation under a microscope.

Even if the petri dish is positioned within a range of approximately 5 μm with the use of the petri dish holder, it is impossible to position a cell located out of a center within a range of about 5 μm, because the round petri dish cannot controlled in the rotation direction.

Thus, during the long-term observation requiring the exchange of the culture medium, the specific cell practically cannot be observed immediately before and after the exchange of the culture medium.

SUMMARY OF THE INVENTION

An observation apparatus according to one aspect of the present invention includes a sample tray that holds a container housing a cultured cell and a culture medium and covered with a lid; an observation unit that serves for observation of the cultured cell; and a shifting unit that relatively shifts the sample tray and a light axis of the observation unit along a plane that is orthogonal to the light axis of the observation unit, and the sample tray includes a container holding unit that holds the container by utilizing an elastic force, and at least one of the lid and one portion of the lid is made detachable, with the container being held in the sample tray by the container holding unit.

According to the present invention, the observation apparatus is provided, which allows for an observation of a specific cell even immediately before and after the culture medium exchanges with a good positional reproducibility.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of the present invention will be described in detail below with reference to the accompanying drawings.

Figure 1:
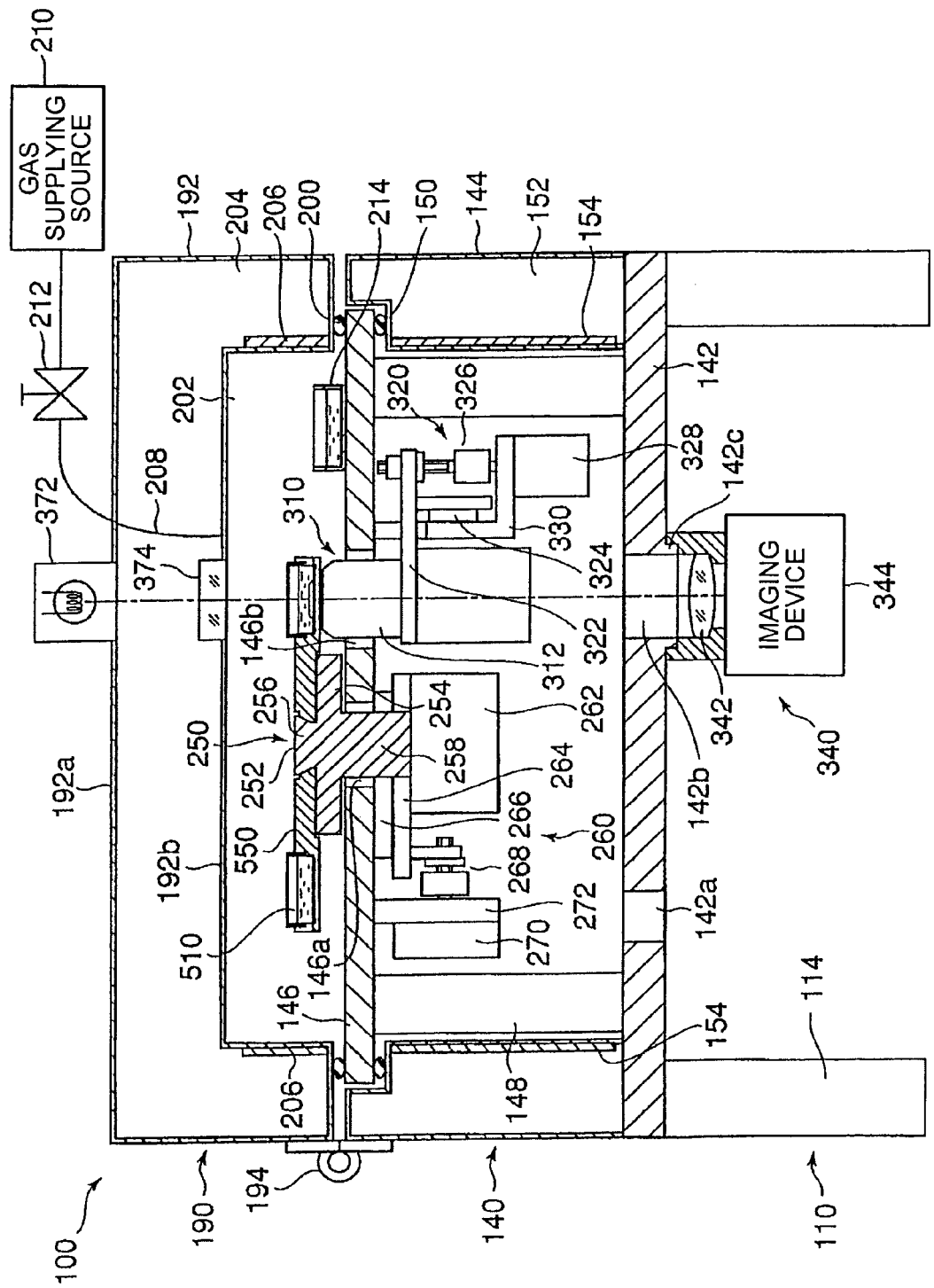
FIG. 1 is a schematic sectional view of a culture observation apparatus according to a first embodiment of the present invention.

A first embodiment is directed to a culture observation apparatus for culturing and observing a cell in culture. The culture observation apparatus basically includes a culture device (incubator) used for culturing a sample and a microscope used for observing the sample, which are combined with each other. FIG. 1 is a schematic sectional view of a culture observation apparatus according to the first embodiment of the present invention.

As shown in FIG. 1, the culture observation apparatus 100 includes a culture device main body 190, a culture device sub-main body 140, and a main-body supporting base 110 that supports these.

The main-body supporting base 110 has a plurality of leg members 114.

The culture device sub-main body 140 is provided with a lower base portion 142 that is supported by the leg members 114, a side wall 144 that surrounds the upper periphery of the lower base portion 142, and an upper base portion 146 that covers an opening on the upper side of the side wall 144.

The upper base portion 146 is supported by a plurality of supporting pillars 148 that stand on the lower base portion 142. The upper base portion 146 and the side wall 144 are made in contact with each other through a seal member 150, with a gap between these being kept in an air-tight state. The side wall 144 has a hollow structure including a heat-insulating space 152, and a heater 154 is installed inside the heat-insulating space 152 of the side wall 144.

The lower base portion 142 has a through hole 142a having a diameter of about 30 mm, which allows the inner space of the culture device sub-main body 140 to communicate with outside air.

The culture device main body 190 is provided with a box-shaped case member 192 with an opening on the bottom face. The case member 192 is attached to the side wall 144 by hinges 194 so as to be opened and closed with respect to the culture device sub-main body 140. A seal member 200 is placed between the case member 192 and the upper base portion 146, and when closed, the case member 192 is made in contact with the upper base portion 146 through the seal member 200, with a gap between the case member 192 and the upper base portion 146 being kept in an air-tight state. The case member 192 has a hollow structure including a heat-insulating space 204, and a heater 206 is installed inside the heat-insulating space 204 of the case member 192.

When the case member 192 is closed, the culture device sub-main body 140 and the culture device main body 190 are allowed to form a culture space 202 used for culturing a sample.

A gas supplying flow path 208, used for supplying a gas such as a carbon dioxide gas to the culture space 202, is connected to the case member 192. The gas supplying flow path 208 is connected to a gas supplying source 210, and a valve 212 used for controlling the amount of supply of the gas is installed in the middle of the gas supplying flow path 208.

The culture observation apparatus 100 is provided with a tray attaching unit 252 to which a sample tray 550 is attached and a horizontal shifting mechanism 260 used for shifting the tray attaching unit 252 horizontally inside the culture space 202.

The tray attaching unit 252 has a tray receiving unit 254 that receives the sample tray 550, a protruding portion 256 that protrudes upward from the tray receiving unit 254 and a rotation shaft 258 that extends downward from the tray receiving unit 254. The rotation shaft 258 is rotatably supported by a mechanism not shown.

The upper base portion 146 has a through hole 146a, and the rotation shaft 258 of the tray attaching unit 252 extends through the through hole 146a of the upper base portion 146. A gap between the upper face of the upper base portion 146 and the lower face of the tray receiving unit 254 is preferably set to 0.1 mm or less in order to preferably suppress a leak of moisture. Moreover, in order to further suppress the leak of moisture, an elastic member may be placed between the upper face of the upper base portion 146 and the lower face of the tray receiving unit 254.

The horizontal shifting mechanism 260 is provided with a motor 262 used for rotating the tray attaching unit 252, a motor supporting member 264 that supports the motor 262, a linear guide 266 that shiftably supports the motor supporting member 264, a ball screw 268 that is engaged with the motor supporting member 264, a motor 270 used for driving the ball screw 268, and a motor supporting member 272 that supports the motor 270.

The motor supporting member 264 is attached to the upper base portion 146 through the linear guide 266, and allowed to shift laterally with respect to the upper base portion 146. Here, the motor supporting member 272 is secured to the upper base portion 146. Moreover, the ball screw 268 converts a rotation movement of the shaft of the motor 270 to a linear movement of the motor supporting member 264.

The microscope, which is an observation unit of the culture observation apparatus, is provided with an objective optical unit 310 and an image-forming optical unit 340. The objective optical unit 310 is housed inside the culture device sub-main body 140. The image-forming optical unit 340 is placed on a lower outer portion of the culture device sub-main body 140.

The objective optical unit 310 is provided with an objective lens 312 and a focusing mechanism 320 used for shifting the objective lens 312 upward and downward.

The focusing mechanism 320 is provided with an objective lens supporting member 322 that supports the objective lens 312, a linear guide 324 that shiftably supports the objective lens supporting member 322, a ball screw 326 that is engaged with the objective lens supporting member 322, a motor 328 used for driving the ball screw 326, and a motor supporting member 330 that supports the motor 328.

The motor supporting member 330 is secured to the upper base portion 146. The objective lens supporting member 322, which is attached to the motor supporting member 330 through the linear guide 324, is capable of shifting upward and downward with respect to the motor supporting member 330. The ball screw 326 converts a rotation movement of the shaft of the motor 328 to a linear movement of the objective lens supporting member 322.

The upper base portion 146 has a through hole 146b, and the objective lens 312 extends through the through hole 146b of the upper base portion 146. A gap between the through hole 146b of the upper base portion 146 and the objective lens 312 is preferably set to 0.1 mm or less in order to preferably suppress a leak of moisture. Moreover, in order to further suppress the leak of moisture, an elastic member may be placed between the through hole 146b of the upper base portion 146 and the objective lens 312.

The image-forming optical unit 340 is provided with an image-forming lens 342 and an imaging device 344. The lower base portion 142 has a through hole 142b, and the image-forming optical unit 340 is optically coupled to the objective lens 312 through the through hole 142b of the lower base portion 142. Moreover, the lower base portion 142 has an image-forming optical unit attaching unit 142c, and the image-forming optical unit 340 is attached to the image-forming optical unit attaching unit 142c.

Moreover, the microscope is provided with a transmissive lighting optical system used for providing transmissive lighting of the sample 510. The transmissive lighting optical system is provided with an illuminating light source 372 that is attached to an outer wall 192a of the case member 192 in a tightly-sealed state, and an optical window 374 that is formed in an inner wall 192b of the case member 192 in a tightly-sealed state. Both of the illuminating light source 372 and the optical window 374 are located above the objective lens 312.

The illuminating light source 372 emits illuminating light, and the optical window 374 allows the illuminating light to pass therethrough.

Moreover, the microscope is provided with an excitation lighting optical system used for exciting the sample 510, though not shown in the drawings.

Figure 2:
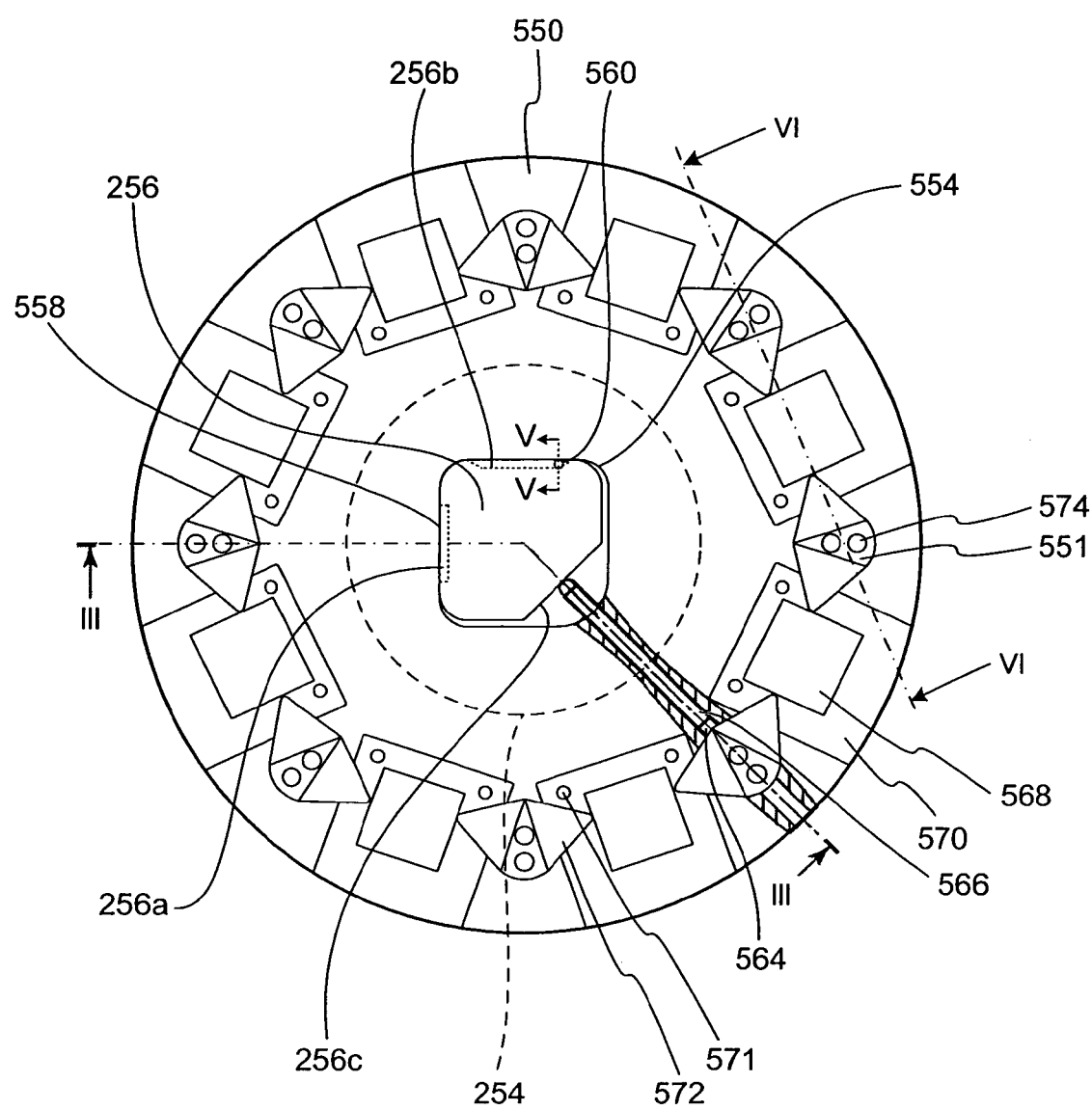
FIG. 2 is a plan view of a sample tray shown in FIG. 1.
Figure 3:
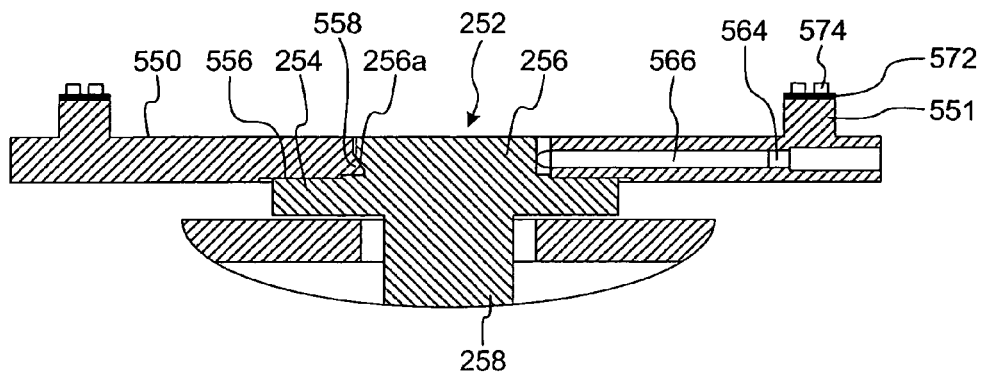
FIG. 3 is a sectional view taken along line III-III of FIG. 2.
Figure 4:
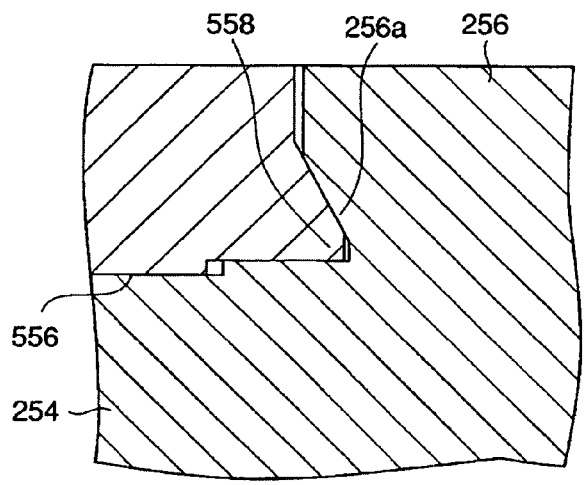
FIG. 4 is a partial enlarged view of the section shown in FIG. 3.
Figure 5:
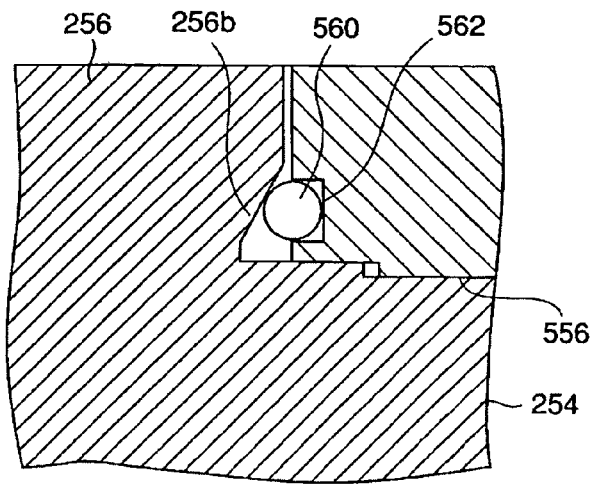
FIG. 5 is a sectional view taken along line V-V of FIG. 2.

FIG. 2 is a plan view of the sample tray shown in FIG. 1. FIG. 3 is a sectional view taken along line III-III of FIG. 2. FIG. 4 is an enlarged view of one portion of FIG. 3. FIG. 5 is a sectional view taken along line V-V of FIG. 2.

As shown in FIG. 2, the tray receiving unit 254 of the tray attaching unit 252 has a round shape, and the upper face thereof is orthogonal to the light axis of the objective lens 312. The protruding portion 256 of the tray attaching unit 252 has a substantially pentagonal shape. The protruding portion 256 has two male dovetails 256a and 256b that are respectively formed on the two side faces adjacent with each other. Each of the male dovetails 256a and 256b has a slope that tilts outward at approximately 60degrees. Moreover, the protruding portion 256 is provided with a pressing face 256c that is different from the two side faces respectively having the male dovetails 256a and 256b. The pressing face 256c is substantially orthogonal to the bisector of each of the two side faces having the respective male dovetails 256a and 256b.

The sample tray 550 is provided with an opening 554 that has a substantially rectangular shape and is formed in the center, and a depressed plane 556 that has a round shape (see FIG. 3) and is formed on the bottom face outside of the opening 554. The opening 554 is larger than the protruding portion 256 so that the protruding portion 256 is allowed to pass through the opening 554. The depressed plane 556 is larger than the tray receiving unit 254 so that the upper face of the tray receiving unit 254 can be made in face-contact with the depressed plane 556.

As shown in FIGS. 3 and 4, the sample tray 550 is provided with a female dovetail 558 that is made in face-contact with the male dovetail 256a of the protruding portion 256, and formed on the side face of the opening 554 that faces the male dovetail 256a of the protruding portion 256.

As shown in FIG. 5, the sample tray 550 also has a depressed portion 562 that receives a ball 560 that is placed in contact with the male dovetail 256b, and formed on the side face of the opening 554 that faces the male dovetail 256b of the protruding portion 256.

As shown in FIGS. 2 and 3, the sample tray 550 is provided with a female screw 564 that extends between the outer peripheral side face and the side face of the center opening 554, and a fixed screw 566 that is meshed with the female screw 564. The female screw 564 and the fixed screw 566 form pressing means that press the pressing face 256c of the protruding portion 256.

The sample tray 550 is attached to the tray attaching unit 252 in the following manner.

The sample tray 550 is mounted on the tray attaching unit 252 with the fixed screw 566 drawn therein. In this state, the bottom face of the sample tray 550 is made in face-contact with the tray receiving unit 254, with the protruding portion 256 being positioned inside the opening 554 of the sample tray 550. The fixed screw 566 is bolted to be pressed against the pressing face 256c. The sample tray 550 is shifted by the resulting reaction force, and pushed against the protruding portion 256.

The fixed screw 566 is bolted appropriately so that the sample tray 550 is secured onto the tray attaching unit 252. In this state, by an interaction between the male dovetail 256a and the female dovetail 558 as well as by an interaction among the male dovetail 256b, the ball 560, and the depressed portion 562, the depressed plane 556 of the sample tray 550 is positively pushed against the upper face of the tray receiving unit 254 so that the sample tray 550 is maintained horizontally. In other words, the sample tray 550 is placed in such a manner that the upper face thereof is made in parallel with the plane that is orthogonal to the light axis of the objective lens 312. Moreover, since the sample tray 550 is made in contact with the tray attaching unit 252 through one face of the female dovetail 558 and the ball 560, the sample tray 550 is always secured onto the tray attaching unit 252 with good reproducibility.

Figure 6:
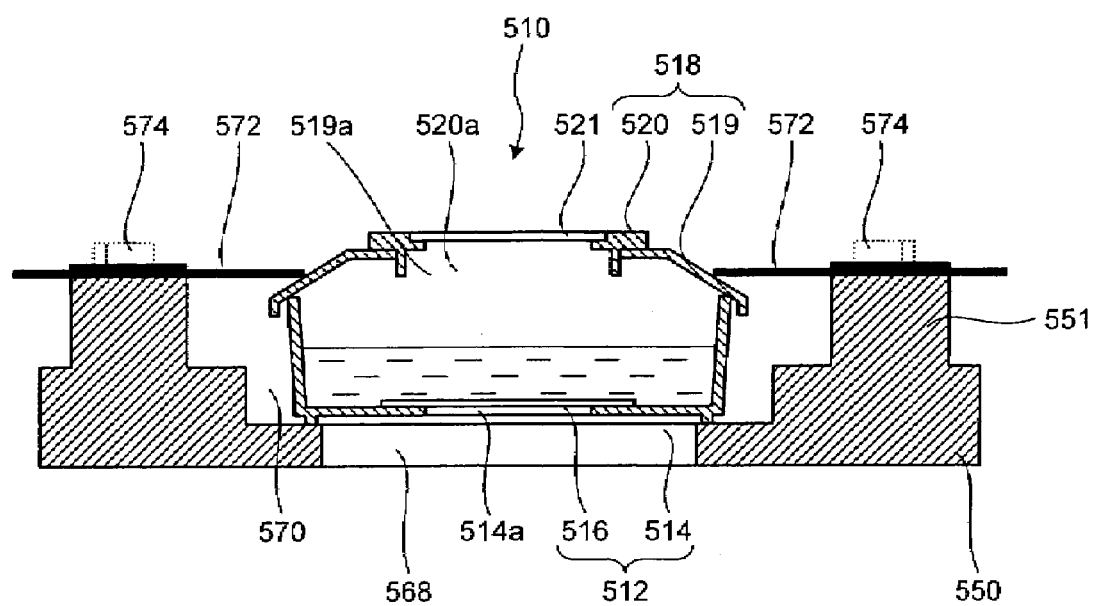
FIG. 6 is a sectional view taken along line VI-VI of FIG. 2.

FIG. 6 is a sectional view taken along line VI-VI of FIG. 2. FIG. 6 includes the sample 510 drawn together with the apparatus.

As shown in FIG. 6, the sample 510 includes a container 512 that houses a cultured cell and a culture medium, and a lid 518 that covers the container 512. The container 512 is optically transparent.

The container 512 includes a container main body 514 and a cover glass 516. The container main body 514 is a Schale-shaped plastic container having a diameter of 35 mm, with an opening 514a having a diameter of about 10 mm formed in the bottom portion. The cover glass 516 is a cover glass having a thickness of 0.17 mm, which has been widely used in the microscope field, and closes the opening 514a of the bottom portion of the container main body 514.

The objective lens 312 requires a high NA for brightness and resolution. In general, an objective lens with a high NA is optimally designed to be used with a cover glass having a thickness of 0.17 mm. Since the container 512 has a cover glass of 0.17 mm in thickness at a portion facing the objective lens 312, a generally-used objective lens with a high NA can be used as the objective lens 312.

As shown in FIG. 2, the sample tray 550 has a plurality of openings 568 that allow observation through the objective lens 312 from below and depressed portions 570 formed around respective openings 568. The openings 568 are positioned along a circumference with a diameter of approximately 160 mm substantially from a center of the sample tray 550. The opening 568 has, for example, a shape close to a square, with each side being set to approximately 25 mm, and is designed to such a size that, with respect to relative shifts of the sample tray 550 and the objective lens 312, the two members are prevented from interfering with each other. The depressed portion 570 has a shape close to a square with each side being set to approximately 40 mm, and the container 512 can be mounted thereon. The container 512 is placed inside the depressed portion 570 so that the depressed portion 570 supports the container 512. Moreover, each depressed portion 570 is provided with two protrusions 571, which, when the container 512 is mounted on the depressed portion 570, are made in contact with the container 512 to serve as stoppers that perform positioning.

The sample tray 550 is provided with a container holding mechanism that holds the container 512 and is located between the protruding sections 570. The container holding mechanism is provided with a container holding member 572 made of a plate spring, and fixed screws 574 used for attaching the container holding member 572 to the sample tray 550.

Moreover, the container holding member 572 is secured to the upper portion of a holding member attaching unit 551, which is provided between the protruding sections 570, with the fixed screws 574. The holding member attaching unit 551 is allowed to protrude from the surface of the sample tray 550 so as to maintain the container holding member 572 at an appropriate height so as to secure the container 512 and the lid 519. Here, the container holding member 572 made of the plate spring and the surface of the sample tray 550 are made substantially in parallel with each other.

As shown in FIG. 6, the lid 518 includes an edge portion 519 and a center portion 520, and the edge portion 519 and the center portion 520 can be separated from each other. The center portion 520 has an opening 520a with a cover glass 521 being fixed thereon in a manner so as to cover the opening 520a. Moreover, the edge portion 519 has an opening 519a so that, when the center portion 520 is attached to the edge portion 519, the center portion 520 plugs the opening 519a.

The peripheral portion of the opening 519a of the edge portion 519 is processed into a tapered shape that expands downwards, and the container holding member 572 is designed to press the portion of the edge portion 519 formed into the tapered shape. With this arrangement, the container holding member 572 allows the container 512 and the lid 518 to be maintained on the sample tray 550 in a stable manner.

Upon securing the container 512 and the lid 518, in a state where the lid 518 is mounted on the container 512, the container 512 and the lid 518 are inserted onto the depressed portion 570 from the outer peripheral side of the sample tray 550. In this case, the container 512 and the lid 518 are inserted onto the depressed portion 570 until the container 512 comes into contact with the protrusions 571. In the state where the container 512 is in contact with the protrusions 571, the container holding members 572 on two sides are allowed to press the edge portion 519 of the lid 518 in a diameter direction so that it becomes possible to prevent the container 512 and the lid 518 from jumping outside of the depressed portion 570 or from moving on the depressed portion 570. Here, when the container 512 and the lid 518 are inserted onto the depressed portion 570, the center portion 520 may be attached to the edge portion 519 or may be removed therefrom.

The container holding member 572 is designed so that the center portion 520 of the lid 518 can be removed, when the edge portion 519 of the lid 518 is pressed with the container 512 and the edge portion 519 of the lid 518 being held on the sample tray 550. For this reason, for example, upon exchanging culture mediums, the culture mediums can be exchanged with only the center portion 520 of the lid 518 being removed. In other words, operations such as the exchanging operation of culture mediums can be carried out without shifting the position of the container 512. Here, the container holding member 572, shown in FIGS. 2 and 6, has a shape extending toward the depressed portions 570 on two sides from one holding member attaching unit 551; however, the container holding member 572 is not intended to be limited to this structure.

As shown in FIG. 1, upon using the culture observation apparatus 100, the sample tray 550 holding a plurality of samples 510 is attached to the tray attaching unit 252, and a moisturing pad 214 containing pure water is placed in the culture space 202. The culture space 202 is controlled to 37° C. in its inside temperature by the heater 206, and also to 5% in its carbon dioxide concentration by the valve 212. The inner space of the culture device sub-main body 140 is controlled to 37° C. in its inside temperature by the heater 154.

Since the culture space 202 is hardly influenced by the outside air by the heat-insulating space 204 of the case member 192, and since the inner space of the culture device sub-main body 140 is kept at 37° C., the inner temperature of the culture space 202 is favorably maintained at 37° C. Moreover, since the moisture generated in the culture space 202 is hardly leaked outside, the inside of the culture space 202 is maintained at a high moisture state close to 100%.

Since the through hole 142a that connects the inner space of the culture device sub-main body 140 to the outside space has a small diameter, only a little outside air is allowed to flow into the culture device sub-main body 140. Moreover, since the inner space of the culture device sub-main body 140 is enclosed by the heat-insulating space 152, it is hardly influenced by the outside air. For this reason, the objective lens 312 and the focusing mechanism 320, placed inside the culture device sub-main body 140, are desirably maintained at 37° C. without being influenced by the outside air. When the objective lens 312 and the focusing mechanism 320 are influenced by temperatures, defocusing tends to occur easily; however, since this structure maintains the temperature of the objective lens 312 and the focusing mechanism 320 at a constant temperature, it is possible to favorably prevent the occurrence of defocusing.

Even if slight moisture invades inside the culture device sub-main body 140 from the culture space 202, since the moisture is diffused into the outside air through the through hole 142a, the inside of the culture device sub-main body 140 is maintained at a low level of moisture. Consequently, it becomes possible to prevent the objective lens 312 from dew condensation and also to prevent the focusing mechanism 320 from rusting.

Upon observation, the sample 510 located above the objective lens 312 is observed. The sample 510 to be observed can be switched with the substantial rotation of the sample tray 550 by the horizontal shifting mechanism 260. The observation site within the sample 510 is adjusted by the shift of the sample tray 550 along the plane orthogonal to the light axis of the objective lens 312 by the horizontal shifting mechanism 260. This adjustment is achieved through the combination of the rotation and the translational shift of the sample tray 550. The rotation and the translational shift are carried out within a range in which the tip of the objective lens 312, located inside the opening 568, is kept from contacting the sample tray 550.

In the first embodiment, the diameter of the container 512 is 35 mm, and eight samples 510 are arranged on the sample tray 550 along the circumference having a diameter of 160 mm. Since the switching process of the samples 510 is carried out by the rotation of the sample tray 550, no translational shift of the sample tray 550 is required to switch the samples 510. Although the sample tray 550 is translation-shifted so as to adjust the observation position, the amount thereof is limited to approximately 10 mm. Therefore, there is only a little space that allows the sample tray 550 to shift.

The following description will discuss a comparative example in which nine samples 510 are arranged in a lattice format with longitudinal and lateral positions of 3×3, and switched by using X and Y stages. In this case, translational shifts of the X and Y stages of 80 mm or more are required for the respective X and Y directions. In contrast, in the first embodiment, the sample tray 550 requires no translational shift for switching the samples 510, and only the translational shift of approximately 10 mm is required for the adjustment of the observation position. Therefore, in comparison with the device using the X and Y stages, the space required for the switching of the samples 510 and the adjustment of the observation position is reduced greatly. This is advantageous in achieving a small-size apparatus at low costs.

Moreover, upon carrying out a long-term observation, an exchange of culture mediums is required. The exchange of culture mediums is carried out with each of the sample trays 550 being removed from the tray attaching unit 252. In other words, during the exchange of culture mediums, the container 512 and the edge portion 519 of the lid 518 are maintained on the sample tray 550, and firmly secured by the container holding mechanism so that no positional deviations occur.

After the exchange of culture mediums, the sample tray 550 is attached again to the tray attaching unit 252 in the same state as the state before the exchange of culture mediums.

In this manner, the first embodiment makes it possible to exchange culture mediums without the necessity of removing the container 512 and the edge portion 519 of the lid 518 from the sample tray 550 and also to attach the sample tray 550 to the tray attaching unit 252 with good positional reproducibility; therefore, the container 512 is properly placed at the original position. Thus, it becomes possible to observe a specific cell for a long time.

In the first embodiment, the case member 192 can be opened and closed with respect to the culture device sub-main body 140; however, not limited to this structure, the case member 192 may be secured to the culture device sub-main body 140. In this case, the case member 192 is required to have an opening formed on a side face and a lid for closing the opening of the side wall so as to bring in and take out the sample tray 550 and a moisturing pad 214. Moreover, the case member 192 may be designed so that one portion of the bottom has an opening with the opening being closed when it is attached to the culture device sub-main body 140.

Figure 7:
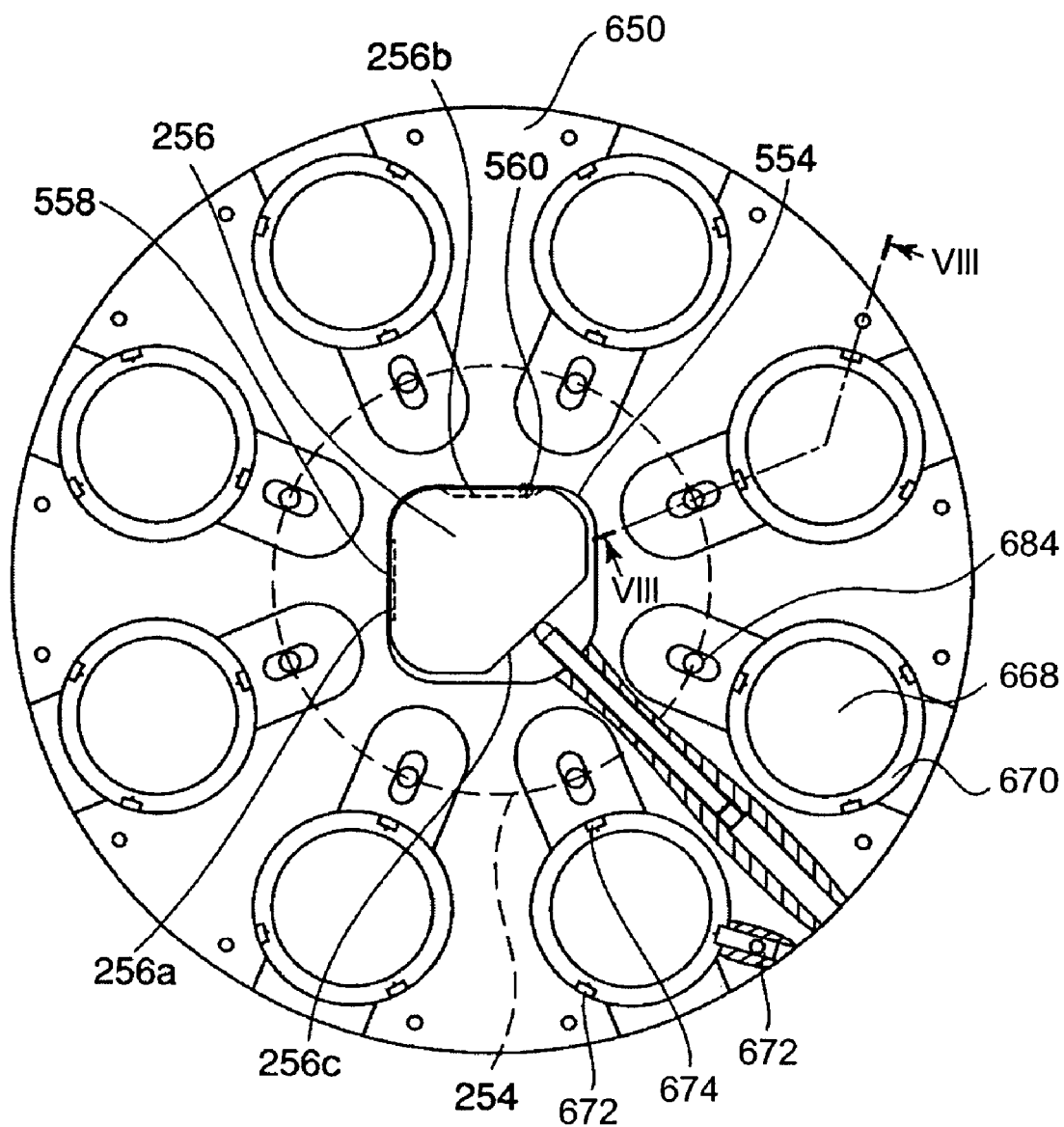
FIG. 7 is a plan view of a sample tray employed in a culture observation apparatus according to a second embodiment of the present invention.
Figure 8:
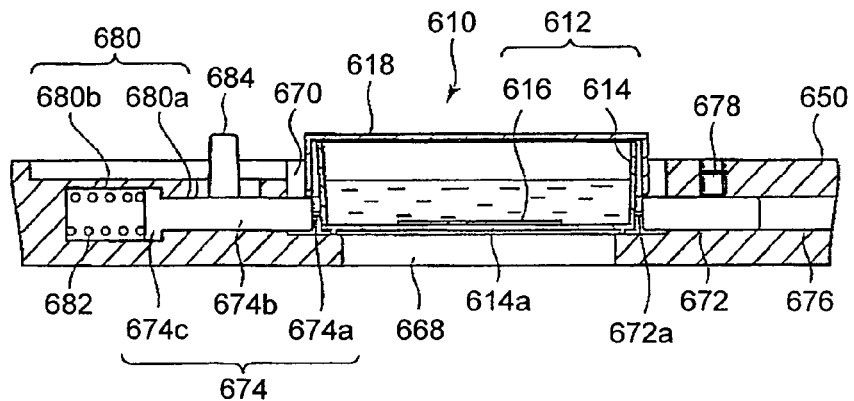
FIG. 8 is a sectional view taken along line VIII-VIII of FIG. 7.

A second embodiment is directed to a sample tray 650 that can replace the sample tray 550 according to the first embodiment. FIG. 7 is a plan view of a sample tray in accordance with the second embodiment of the present invention. FIG. 8 is a sectional view taken along line VIII-VIII of FIG. 7. In FIG. 8, a sample is drawn together with the sample tray. In FIGS. 7 and 8, the same elements as the elements according to the first embodiment are denoted by the same reference characters as in the first embodiment.

As shown in FIG. 8, a sample 610 includes a container 612 that houses a cultured cell and a culture medium and a lid 618 that covers the container 612. Both of the container 612 and the lid 618 are optically transparent.

The container 612 includes a container main body 614 and a cover glass 616. The container main body 614 is a Schale-shaped plastic container having a diameter of 35 mm, with an opening 614a having a diameter of about 10 mm formed in the bottom portion. The cover glass 616 is a cover glass having a thickness of 0.17 mm, which is widely used in the microscope field, and is allowed to plug the opening 614a of the bottom portion of the container main body 614.

As shown in FIG. 7, the sample tray 650 has a plurality of openings 668 that allow observation through the objective lens 312 from below and depressed portions 670 formed around respective openings 668. The openings 668 are positioned along the circumference with a diameter of approximately 160 mm substantially from a center of the sample tray 650. The opening 668, which has a diameter of approximately 25 mm, has such a size that, with respect to relative shifts of the sample tray 650 and the objective lens 312, the two members are prevented from intervening with each other. The diameter of the depressed portion 670 is approximately 40 mm, which is slightly larger than the diameter of the container 612. The container 612 is placed inside the depressed portion 670 so that the depressed portion 670 supports the container 612.

Moreover, the sample tray 650 is provided with a container holding mechanism used for holding the container 612 on each of the depressed portions 670. The container holding mechanism is provided with two fixed container holding members 672, a shiftable container holding member 674, and a coil spring 682 that is pressing the container holding member 674.

Two container holding members 672 and the single container holding members 674 are placed around the depressed portion 670 at equal intervals, that is, with an angular interval of 120 degrees. The container holding member 672 has a contact portion 672a that is made in contact with the container 612, and the contact portion 672a has a sharp tip. The tip of the contact portion 672a has, for example, a diameter of about 50 µm. Moreover, the container holding member 674 has a contact portion 674a that is made in contact with the container 612, and the contact portion 674a has a sharp tip. The tip of the contact portion 674a has, for example, a diameter of about 50 µm.

The container holding member 672, which has a column shape, is housed into a hole 676 that is formed in the sample tray 650, and secured by a fixed screw 678. The securing position of the container holding member 672 is changeable, and adjusted in accordance with the size of the container 612.

The container holding member 674 is provided with a column-shaped main-body portion 674b, and an end portion 674c having a column shape that has a size larger than the main-body portion 674b. The container holding member 674 is housed in a hole 680 formed in the sample tray 650, and allowed to freely shift inside the hole 680. The hole 680 has a small-diameter portion 680a and a large-diameter portion 680b so that the main-body portion 674b of the container holding member 674 is housed in the small-diameter portion 680a and the end portion 674c of the container holding member 674 is housed in the large-diameter portion 680b. A coil spring 682 is arranged inside the large-diameter portion 680b, and the coil spring 682 presses the end portion 674c. A knob 684 is secured to the main-body portion 674b of the container holding member 674, and the knob 684 protrudes from the upper face of the sample tray 650. With the manipulation of the knob 684, the container holding member 674 can be shifted against the elastic force of the coil spring 682.

Upon securing the container 612, the container holding member 674 is retreated by the manipulation of the knob 684, and after the container 612 is placed on the bottom of the depressed portion 670, the knob 684 is released. Thus, the container 612 is pressed by the container holding member 674, and made in contact with the two container holding members 672. Since the container holding member 674 continues to press the container 612 by a predetermined force that is determined by the coil spring 682, the container 612 is held by the two container holding members 672 and the single container holding member 674.

Since both of the contact portion 672a of the container holding member 672 and the contact portion 674a of the container, holding member 674 have a tip having a diameter of about 50 µm, these contact portions cut into the container 612. For this reason, though the container 612 has a shape expanding upward from the bottom face, it is positively held without being push and displaced upward. With this arrangement, upon removing the lid 618 from the container 612 for the exchange of culture mediums or the like, the container 612 is prevented from unexpectedly moving and rotating. In other words, the operations such as exchanging culture mediums can be carried out without the necessity of shifting the position of the container 612. Moreover, since the portion close to the bottom face of the container 612 is pressed, the lid of the attached container may also be utilized.

A third embodiment is directed to an observation apparatus used for observing a cultured cell. The observation apparatus is formed by an inverted microscope system.

Figure 9:
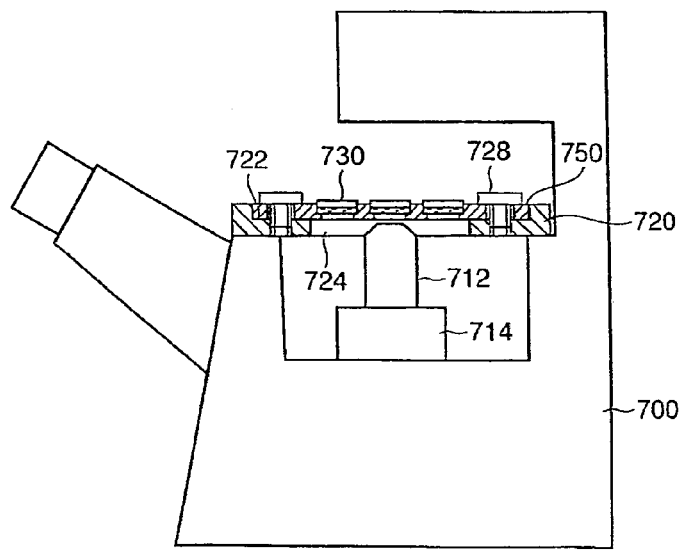
FIG. 9 is a schematic drawing of an observation apparatus according to a third embodiment of the present invention.
Figure 10:
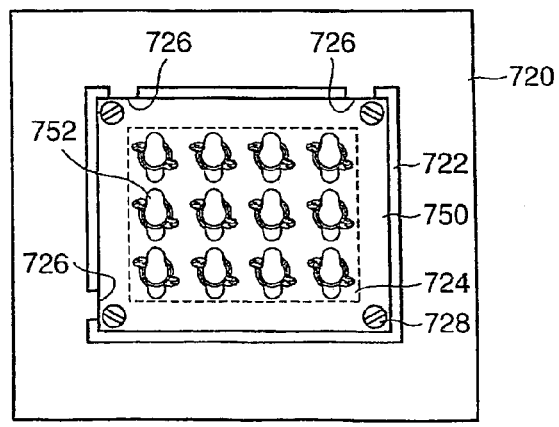
FIG. 10 shows a stage and a sample tray shown in FIG. 9.
Figure 11:
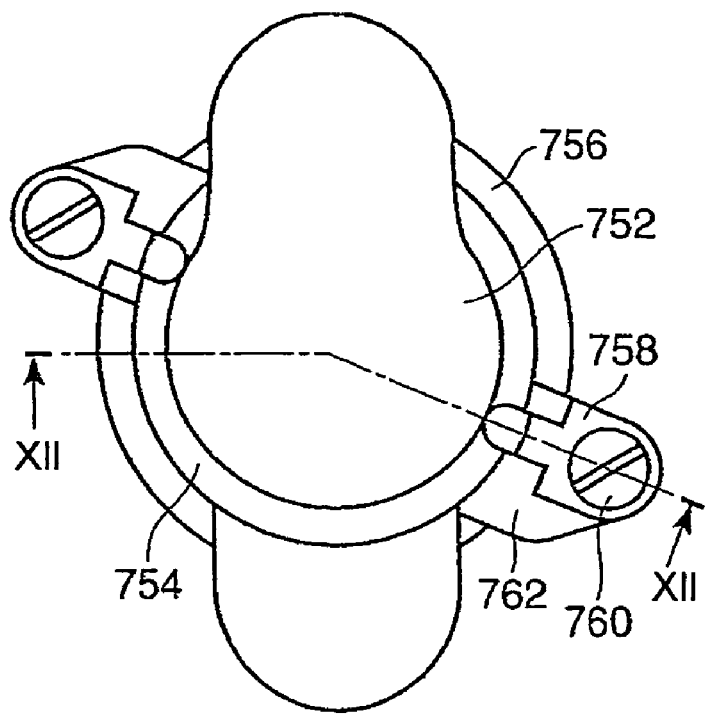
FIG. 11 is a plan view of a container holding mechanism installed in the sample tray.

FIG. 9 schematically shows an observation apparatus in accordance with the third embodiment of the present invention. FIG. 10 shows a stage and a sample tray that are shown in FIG. 9. FIG. 11 is a plan view that shows a container holding mechanism that is installed in the sample tray. FIG.

Figure 12:
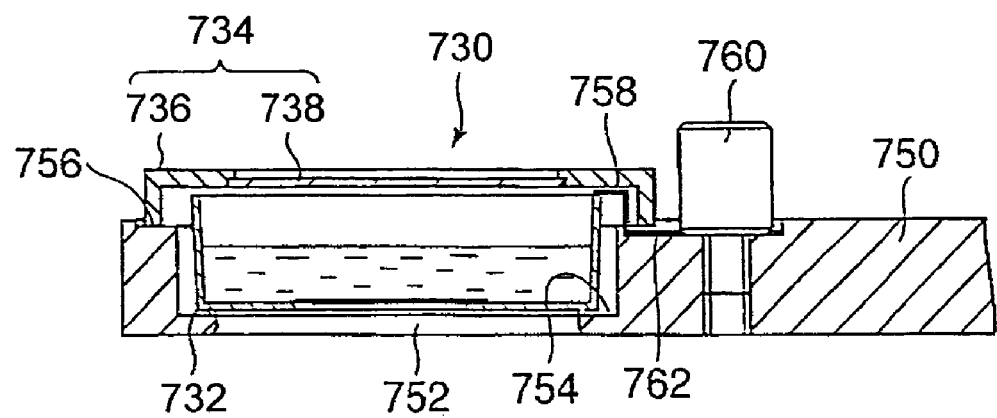
FIG. 12 is a sectional view taken along line XII-XII of FIG. 11.

12 is a sectional view taken along line XII-XII of FIG. 11. In FIG. 12, a sample is also drawn together.

As shown in FIG. 9, a microscope system 700 includes an objective lens 712, a focusing mechanism 714 used for shifting the objective lens 712 upwards and downwards, and a stage 720 on which a sample tray 750 holding a sample 730 is mounted. The stage 720 can be shifted horizontally. The stage 720 is provided with a depressed portion 722 that has a size larger than the sample tray 750 and an opening 724 that has a size smaller than the depressed portion 722.

As shown in FIG. 10, the depressed portion 722 of the stage 720 has contact faces 726 at three positions. When placed in the depressed portion 722 of the stage 720, the sample tray 750 is pressed onto the contact faces 726 at the three positions by the operator to be positioned, and secured onto the stage 720 with four fixed screws 728.

As shown in FIG. 12, the sample 730 includes a container 732 and a lid 734. The lid 734 is provided with a lid main-body 736 having a round opening and a glass plate 738 used for covering the opening of the lid main-body 736. The container 732 has the same structure as the containers 512 and 612 described above in the first embodiment.

As shown in FIG. 10, the sample tray 750 has a rectangular shape, and is provided with openings 752 that allow observation through an objective lens 712 from below. The openings 752 are arranged into a lattice format. Moreover, as shown in FIGS. 11 and 12, the sample tray 750 is provided with depressed portions 754 each formed around the respective openings 752, and a lid mounting face 756 that is formed on the periphery of each depressed portion 754 for each of the openings 752. The container 732 is placed inside the depressed portions 754 so that the depressed portions 754 support the container 732. Here, the lid 734 is mounted on the lid mounting face 756.

Moreover, the sample tray 750 is provided with a container holding mechanism used for holding the container 732, for each of the depressed portions 754. The container holding mechanism includes a plate spring 758 used for pressing the container 732, and a fixed screw 760 for securing the plate spring 758 onto a spring mount face 762 of the sample tray 750. The spring mount face 762 is located at a position lower than the lid mounting face 756. The plate spring 758 is bent into a crank shape, and extends between the container 732 and the lid 734 so that the resulting pressing force is applied onto the upper face of the container 732. Thus, the container 732 is secured onto the sample tray 750.

In the third embodiment, since the lid 734 is opened and closed without the application of a force onto the plate spring 758, there is no possibility of relative positional deviations of the sample 730 with respect to the sample tray 750 when culture mediums are exchanged. Moreover, since the sample tray 750 is pressed onto the contact faces 726 at the three positions formed in the depressed portion 722 of the stage 720 for the positioning, the sample tray 750 is accurately secured to the original position before the culture medium exchange.

The third embodiment makes it possible to provide an apparatus having a simple shape, and consequently to achieve an inexpensive apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An observation apparatus comprising:
    a sample tray that holds a container adapted to house a cultured cell and a culture medium and covered with a lid;
    an observation unit that serves for observation of the cultured cell;
    a shifting unit that shifts the sample tray relative to a light axis of the observation unit along a plane that is orthogonal to the light axis of the observation unit;
    a tray holding unit that detachably holds the sample tray to the shifting unit with good reproducibility;
    wherein the tray holding unit includes a tray attaching unit to which the sample tray is attached, and the tray attaching unit includes (i) a tray receiving portion that receives the sample tray, and (ii) a protruding portion that protrudes upward from the tray receiving portion, wherein the protruding portion has at least two side faces, each including a male dovetail and a pressing face which extends in a vertical direction and which faces against the at least two side faces; and
    wherein the sample tray includes:
        a flat face that makes face-contact with the tray receiving portion; and
        a depressed portion that is engaged with the protruding portion, the depressed portion including (i) a female dovetail that contacts one of the male dovetails of the protruding portion, (ii) a contact member that contacts the other male dovetail of the protruding portion, and (iii) a pressing unit that presses the pressing face of the protruding portion; and
    a container holding unit that holds the container by utilizing an elastic force, and at least one of the lid and one portion of the lid is made detachable, with the container being held in the sample tray by the container holding unit.

2. The observation apparatus according to claim 1, wherein the container holding unit includes plural container holding members, and each of the container holding members presses an edge of the lid so that a center portion of the lid is made detachable, with the container and the edge of the lid being held on the sample tray.

3. The observation apparatus according to claim 2, wherein a portion of the edge of the lid is processed into a tapered shape, and the container holding member presses the portion of the edge of the lid that is processed into the tapered shape.

4. The observation apparatus according to claim 1, wherein the container holding unit includes plural container holding members, and each of the container holding members includes a contact portion having a sharp tip which contacts the container.

5. The observation apparatus according to claim 1, wherein the container holding unit includes plural container holding members that are supported on the sample tray, and each of the container holding members extends between the container and the lid so as to press the container.

6. The observation apparatus according to claim 1, wherein the contact member is a ball.

* * * * *

UNITED STATES PATENT AND TRADEMARK OFFICE
CERTIFICATE OF CORRECTION

PATENT NO.         : 7,595,188 B2                                Page 1 of 1
APPLICATION NO.    : 11/302591
DATED              : September 29, 2009
INVENTOR(S)        : Hasegawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 936 days.

Signed and Sealed this

Twenty-eighth Day of September, 2010

David J. Kappos
*Director of the United States Patent and Trademark Office*